(12) United States Patent
Wilsak et al.

(10) Patent No.: US 8,530,716 B2
(45) Date of Patent: Sep. 10, 2013

(54) MELT-CRYSTALLIZATION SEPARATION AND PURIFICATION PROCESS

(75) Inventors: Richard A. Wilsak, Naperville, IL (US);
Scott A. Roberts, Naperville, IL (US);
Rose M. Janulis, Oak Brook, IL (US)

(73) Assignee: BP Corporation North America Inc., Houston, TX (US)

( * ) Notice: Subject to any disclaimer, the term of this patent is extended or adjusted under 35 U.S.C. 154(b) by 1196 days.

(21) Appl. No.: 12/191,745

(22) Filed: Aug. 14, 2008

(65) Prior Publication Data

US 2010/0041936 A1 Feb. 18, 2010

(51) Int. Cl.
*C07C 7/14* (2006.01)
(52) U.S. Cl.
USPC ............................ 585/812; 585/815; 585/814
(58) Field of Classification Search
None
See application file for complete search history.

(56) References Cited

U.S. PATENT DOCUMENTS

| | | | |
|---|---|---|---|
| 1,182,773 A | 6/1931 | Cannon | |
| 2,377,915 A | 4/1941 | Gunness | |
| 2,488,031 A | 7/1941 | Gunness | |
| 2,394,814 A | 12/1941 | Snuggs | |
| 2,428,691 A | 6/1944 | Tyson | |
| 2,472,377 A | 1/1945 | Keith | |
| 2,718,308 A | 5/1950 | Le Bus | |
| 2,663,676 A | 3/1951 | Caldwell et al. | |
| 2,780,663 A | 5/1953 | Gunness | |
| 2,813,781 A | 12/1953 | Mertes | |
| 2,854,494 A | 3/1955 | Thomas | |
| 2,851,161 A | 6/1955 | Dahlstrom et al. | |
| 2,815,364 A * | 12/1957 | Green | 560/78 |
| 2,820,070 A * | 1/1958 | Bennett et al. | 585/813 |
| 2,866,833 A | 12/1958 | Spiller, Jr. | |
| 2,885,431 A | 5/1959 | Tarr | |
| 2,903,343 A | 9/1959 | Weedman | |

(Continued)

FOREIGN PATENT DOCUMENTS

| | | |
|---|---|---|
| EP | 1 308 054 | 2/1973 |
| EP | 0 175 401 | 3/1985 |

(Continued)

OTHER PUBLICATIONS

W.T. Koetsier et al. "Oxygen Induced Fouling in a Xylene Isomerization Reactor Bed," *Catalyst Deactivation*, (G. Delmon et al., eds.), vol. 34, pp. 579-588 (1987).

*Primary Examiner* — Tam M Nguyen
(74) *Attorney, Agent, or Firm* — Kalim S. Fuzail (57) ABSTRACT

Processes for separating a solid from a solids-liquids slurry under conditions that prevent ingress of molecular oxygen are advantageous where the presence of molecular oxygen would otherwise reduce efficiencies, contribute to limited product yields, and potentially compromise safe operation of the process or downstream unit operations. Among the various embodiments disclosed herein, is a process utilizing filter columns as solid-liquid separators in combination with crystallization and reslurry unit operations to recover a product component from an initial feed mixture of miscible components. Embodiments of the disclosed processes may include the separation and purification of a product component using a crystallizer in series with a filter column followed by a chemical reactor, using a reslurry drum in series with a filter column, and using a combination of crystallizers and/or reslurry drums in series with at least one filter column. The use of filter columns in such processes is particularly attractive because these columns, when operated under the conditions disclosed herein, limit the undesirable ingress of molecular oxygen into the various process streams, and further improve process efficiencies related to both product component recovery and operating costs.

14 Claims, 3 Drawing Sheets

(56) References Cited

U.S. PATENT DOCUMENTS

| | | | |
|---|---|---|---|
| 3,177,265 | A | 4/1965 | Lammers |
| 3,217,942 | A | 11/1965 | Humbert, Jr. et al. |
| 3,277,200 | A * | 10/1966 | Smith et al. .................. 585/812 |
| 3,319,437 | A | 5/1967 | Goins |
| 3,469,369 | A | 9/1969 | Helmke |
| 3,524,548 | A | 8/1970 | McDonald et al. |
| 3,696,930 | A | 10/1972 | Tokura |
| 3,723,558 | A * | 3/1973 | Kramer ........................ 585/814 |
| 3,772,998 | A | 11/1973 | Menlgat |
| 3,777,892 | A | 12/1973 | Thijssen et al. |
| 3,804,915 | A * | 4/1974 | Schmid et al. ................ 585/801 |
| 3,992,298 | A | 11/1976 | Davis |
| 4,004,886 | A | 1/1977 | Thijssen et al. |
| 4,008,158 | A | 2/1977 | Davis |
| 4,018,579 | A | 4/1977 | Hofmann |
| 4,053,268 | A | 10/1977 | Kishino |
| 4,093,672 | A | 6/1978 | Sun |
| 4,097,543 | A | 6/1978 | Haag et al. |
| 4,117,026 | A | 9/1978 | Haag et al. |
| 4,247,310 | A | 1/1981 | Borst |
| 4,270,937 | A | 6/1981 | Adler et al. |
| 4,332,599 | A | 6/1982 | Thijssen et al. |
| 4,341,085 | A | 7/1982 | Nail |
| 4,344,781 | A | 8/1982 | Higgins et al. |
| 4,453,959 | A | 6/1984 | Bishkin |
| 4,517,806 | A | 5/1985 | Korzonas |
| 4,623,372 | A | 11/1986 | Adler et al. |
| 4,687,497 | A | 8/1987 | Owen et al. |
| 4,713,174 | A | 12/1987 | Zievers et al. |
| 4,734,102 | A | 3/1988 | Thijssen et al. |
| 4,735,481 | A | 4/1988 | Lukas et al. |
| 4,735,781 | A | 4/1988 | Thijssen et al. |
| 4,769,219 | A | 9/1988 | Tasker et al. |
| 4,787,985 | A | 11/1988 | Roodenrijs et al. |
| 4,792,391 | A | 12/1988 | Cox |
| 4,902,407 | A | 2/1990 | Chan et al. |
| 4,933,150 | A | 6/1990 | Haddad et al. |
| 4,956,520 | A * | 9/1990 | Flett et al. .................... 585/815 |
| 4,957,625 | A | 9/1990 | Katoh et al. |
| 5,004,860 | A | 4/1991 | Hansen et al. |
| 5,051,194 | A | 9/1991 | Bahr |
| 5,062,862 | A | 11/1991 | Jansen |
| 5,102,544 | A | 4/1992 | Roodenrijis |
| 5,104,519 | A | 4/1992 | Haddad et al. |
| 5,145,497 | A | 9/1992 | Maeda |
| 5,284,992 | A | 2/1994 | Hotier et al. |
| 5,292,434 | A | 3/1994 | Benesi |
| 5,329,060 | A | 7/1994 | Swift |
| 5,387,406 | A | 2/1995 | Ruoff |
| 5,448,005 | A * | 9/1995 | Eccli et al. .................... 585/812 |
| 5,462,351 | A | 10/1995 | Royal |
| 5,498,822 | A * | 3/1996 | Eccli et al. .................... 585/816 |
| 5,565,090 | A | 10/1996 | Gosling et al. |
| 5,589,079 | A | 12/1996 | Park et al. |
| 5,643,468 | A | 7/1997 | Ure |
| 5,663,456 | A | 9/1997 | Zhang et al. |
| 5,707,512 | A | 1/1998 | Koch et al. |
| 5,770,045 | A | 6/1998 | Gosling et al. |
| 6,068,460 | A | 5/2000 | Haarstad et al. |
| 6,341,567 | B1 | 1/2002 | Robertson et al. |
| 6,376,736 | B1 * | 4/2002 | Rutten et al. .................. 585/815 |
| 6,491,871 | B1 | 12/2002 | Fodor et al. |
| 6,521,135 | B1 | 2/2003 | Benesi |
| 6,565,653 | B2 | 5/2003 | Wilsak |
| 6,600,083 | B2 * | 7/2003 | Doyle et al. .................. 585/828 |
| 6,620,243 | B1 | 9/2003 | Bertellotti et al. |
| 6,652,760 | B2 | 11/2003 | Anderson |
| 6,712,982 | B2 | 3/2004 | Bohn et al. |
| 6,730,221 | B2 | 5/2004 | Bohn et al. |
| 7,078,439 | B2 | 7/2006 | Odueyungbo et al. |
| 7,405,340 | B2 * | 7/2008 | Amelse ......................... 585/812 |
| 2002/0107427 | A1 * | 8/2002 | Doyle et al. .................. 585/828 |
| 2003/0127401 | A1 | 7/2003 | Benesi |
| 2005/0056599 | A1 | 3/2005 | Wilsak et al. |
| 2005/0074378 | A1 | 4/2005 | Ruemekorf et al. |
| 2005/0167338 | A1 * | 8/2005 | Miller et al. .............. 208/310 R |
| 2005/0171395 | A1 * | 8/2005 | Huff et al. ..................... 585/819 |
| 2005/0228206 | A1 * | 10/2005 | Amelse ......................... 585/812 |
| 2006/0013748 | A1 | 1/2006 | Nordhoff et al. |
| 2007/0225539 | A1 | 9/2007 | Wilsak et al. |
| 2009/0197878 | A1 | 8/2009 | Commons et al. |

FOREIGN PATENT DOCUMENTS

| | | |
|---|---|---|
| EP | 0 398 437 | 11/1990 |
| EP | 1 353 915 | 7/2002 |
| WO | WO 91/05556 | 5/1991 |
| WO | WO 95/26947 | 10/1995 |

* cited by examiner

MELT-CRYSTALLIZATION SEPARATION AND PURIFICATION PROCESS

BACKGROUND OF THE INVENTION

1. Field of the Disclosure

The disclosure relates generally to processes for separating solids from a solid-liquid slurry, for example in melt-crystallization separation and purification processes. More specifically, the disclosure relates to separation or purification processes that, under certain operating conditions, advantageously prevent ingress of molecular oxygen into the processes. The processes are, therefore, more efficient than, and at least as safe as, conventional processes for separating solids from a solid-liquid slurry.

2. Brief Description of Related Technology

Solid-liquid separation methods are important in a variety of industries, including, but not limited to, the chemical industry, the pharmaceutical industry, and the water and waste treatment industry. Such solid-liquid separation methods vary, and may include, but are not limited to, vacuum or pressure filtration, centrifugation, sedimentation and clarification. In many chemical processes, these solid-liquid separation methods often play a critical role in the manufacture of particular chemical intermediates. For example, para-xylene (p-xylene or pX) is a chemical intermediate that, when purified, is useful for making terephthalic acid. Purification of para-xylene through crystallization has historically required centrifugation to achieve para-xylene purity levels of about 99.7%.

A para-xylene purification process is typically part of a much larger process of manufacturing para-xylene from a hydrocarbon feed containing mixed $C_8$ aromatic hydrocarbons. In that larger process, a hydrated feed is typically dehydrated in a distillation tower. Any oxygen present in the distillation feed typically exits the tower with the overhead water vapor. A dry feed, of course, need not undergo this dehydration step. Following feed dehydration (if any), the dry $C_8$ aromatic hydrocarbons are purified in a process employing various unit operations. The para-xylene lean stream produced by that purification process contains ortho-xylene (o-xylene or oX), meta-xylene (m-xylene or mX), ethylbenzene, and other components. That para-xylene lean stream typically is vaporized and reacted in the presence of a catalyst and hydrogen (in an isomerization reactor) to obtain an equilibrated mixture of xylene isomers (i.e., oX:mX:pX in a weight ratio of 1:2:1), which is then sent to a fractionation section where the $C_8$ aromatic hydrocarbons are separated and sent to the purification process to obtain purified para-xylene.

The introduction of oxygen into the process has been found to deleteriously affect the isomerization part of the process. For example, the presence of oxygen in the feed to the isomerization reactor leads to fouling in the reactor as well as in the upstream heat exchangers. This results in reduced cycle length. At the end of the cycle, the process must be shut down to regenerate the catalyst and de-coke the heat exchangers. The presence of oxygen may be inconsequential in other processes that might use solids-liquids separators. In the process for manufacturing para-xylene from a mixed $C_8$ aromatic hydrocarbon feed, however, it has been found that the absence or minimization of oxygen is important for efficient operation of the process.

The purification of para-xylene typically begins with a predominantly $C_8$ aromatic hydrocarbon feed that typically includes a mixture of ortho-, meta-, and para-xylene isomers, ethylbenzene, some non-aromatic hydrocarbons, and some $C_{9+}$ aromatic hydrocarbons. Typical mixtures of $C_8$ aromatic hydrocarbons generally contain about 22 wt. % para-xylene, about 21 wt. % ortho-xylene, about 47 wt. % meta-xylene, and about 10 wt. % of other constituents (mostly ethylbenzene). Processes to separate these xylene isomers include low temperature crystallization, fractional distillation, and adsorption.

While the common separation techniques of distillation (based on the differential boiling points of mixture components) and adsorption (based on different affinities of mixture components to a solid adsorbent) are often suitable for generic liquid-liquid mixtures, crystallization requires no adsorbent, is more tolerant of various feedstock compositions, and typically requires no costly feedstock pre-treatment. In separating para-xylene from a $C_8$ aromatic hydrocarbon feed, for example, crystallization is often preferred over adsorption and distillation because crystallization does not require a costly adsorbent (as in adsorption processes), and because xylene isomers and ethylbenzene have undesirably similar boiling points (making distillation difficult), but dramatically different melting points. Pure para-xylene freezes at 56° F. (13° C.), pure meta-xylene freezes at −54° F. (−48° C.), pure ortho-xylene freezes at −13° F. (−25° C.), and pure ethylbenzene freezes at −139° F. (−95° C.). Because para-xylene is present in these mixed feed streams in low concentrations, very low temperatures are generally required to effectively recover the para-xylene from these feed streams by crystallization.

As in any chemical process, capital and operating costs will drive decisions on which specific unit operations to employ to obtain satisfactory products and by-products. These decisions, of course, can be complicated and limited by the physical properties of the products and by-products. Moreover, these decisions can be complicated when, for example, the process needs to be designed and operated to avoid introduction (or manufacture) of contaminants. Important considerations for the recovery and purification of para-xylene via crystallization include, for example, operating costs associated with obtaining low temperature refrigeration, and capital costs associated with solid-liquid separation units. Furthermore, and as explained in more detail herein, oxygen is considered a contaminant in para-xylene manufacturing processes inasmuch as oxygen imparts inefficiencies to the processes. Oxygen may also be considered a contaminant in other manufacturing processes employing solid-liquid separation and purification processes.

Consequently, efficient solid-liquid separation and purification processes that also remove oxygen from the unit operations responsible for the separation and purification are desired. Furthermore, efficient solid-liquid separation and purification processes that also minimize or entirely avoid introduction of oxygen into the unit operations responsible for the separation and purification are desired. In the particular context of para-xylene manufacture, efficient processes for recovering and purifying para-xylene that also remove oxygen from the unit operations responsible for the recovery and purification of para-xylene are desired. Furthermore, efficient processes for recovering and purifying para-xylene that also minimize or entirely avoid introduction of oxygen into the unit operations responsible for the recovery and purification of para-xylene are desired.

SUMMARY OF THE INVENTION

As indicated above, it has been found that the absence or minimization of oxygen is important to efficient operation of a para-xylene manufacturing process. Separation units (e.g., centrifuges) were (and are) commonly used to separate paraxylene from other $C_8$ aromatics. Even employing centrifuges, however, can still lead to oxygen ingress. Screen-bowl centrifuges, for example, are operated under a slight positive pressure. Despite that condition, the operation of the centrifuge to purify xylenes, for example, will pull a vacuum on a seal between the pipe feeding the centrifuge and the rotating assembly of the centrifuge. The presence of leaks in the seal will cause air (and the oxygen therein) to enter the centrifuge.

It has now been found that the use of a purification (or separation) process in accordance with the invention limits the ingress of molecular oxygen into various process streams, such as, for example, those streams that feed downstream isomerization reactors in a para-xylene manufacturing process. Accordingly, it has also been found that certain separation steps (utilizing filter columns, for example) can be used in accordance with the invention in para-xylene manufacturing processes without compromising the safety and efficiencies those processes presently provide. The reduction in molecular oxygen provides a variety of benefits not heretofore available to the para-xylene manufacturing process. For example, the reduction will improve the operation of equipment downstream of the separation units, such as the isomerization reactor and any heat exchange equipment disposed between the separation units and the isomerization reactor. The reduction will cause a concomitant decrease in instances of reactor fouling and plugging, and catalyst coking in the reactor. The reduction will also result in less frequent catalyst regeneration and reactor down-time. Furthermore, the reduction will likely avoid instances of fouling and plugging of any heat exchangers disposed between the separation units and the isomerization reactor. These benefits will be manifested in cost efficiencies and improved para-xylene process yields.

The disclosure generally relates to a process that includes separating para-xylene and molecular oxygen from a slurry containing the same and other xylene isomers under conditions that prevent ingress of molecular oxygen into the process. The para-xylene and molecular oxygen preferably are separated from the slurry in a filter column, under conditions that prevent ingress of molecular oxygen into the process, to produce a filter cake containing para-xylene, and to produce a filtrate containing a liquid product component, the liquid product component including a para-xylene lean product.

In another embodiment, the process is a separation process that includes purifying para-xylene from a slurry containing the same and other xylene isomers under conditions that prevent ingress of molecular oxygen into the separation process, to produce a para-xylene lean product, and isomerizing the para-xylene lean product of the separation. The para-xylene preferably is purified from the slurry in a filter column, under conditions that prevent ingress of molecular oxygen into the separation process, to produce a filter cake containing para-xylene and a filtrate containing a liquid product component, the liquid product component including the para-xylene lean product.

It has been found that a filter column operated under the conditions specified herein will minimize the molecular oxygen content of the filtrate which, in turn, will help prevent undesirable catalyst coking, and fouling and plugging in the isomerization unit. For example, and as described in more detail below, a filter column operated at least at ambient pressure, and preferably at pressures exceeding ambient pressure (e.g., about 2 pounds per square inch (psig) to about 30 psig), will minimize the molecular oxygen content of the filtrate. In highly preferable operation, the filter column is operated at an elevated pressure of at least about 0.5 pounds per square inch (psi) in excess of ambient pressure (i.e., at least about 0.5 psig), even more preferably at least about 1.5 psi in excess of ambient pressure, still more preferably at least about 3 psi in excess of ambient pressure, even more preferably at least about 5 psi in excess of ambient pressure, still more preferably at least about 10 psi in excess of ambient pressure, and further more preferably at least about 15 psi in excess of ambient pressure. A highly preferred pressure range for operating the filter column is about 1.5 psi to about 3 psi in excess of ambient pressure (i.e., about 1.5 psig to about 3 psig). While a pressure exceeding ambient pressure is a condition necessary to ensuring minimum or no molecular oxygen ingress, a pressure too far in excess of ambient pressure will unnecessarily drive operating expenses of the process to a level where the economic benefits of the process may be lost. Furthermore, the vessel used to perform the separation will have a not-to-exceed pressure rating that effectively sets an upper limit on the operable pressure, which, in most cases will not be approached, though is nevertheless suitable. Consequently, close observation of the pressure should be maintained to enjoy the many benefits made possible by the findings presented herein.

To further avoid the damaging effects of molecular oxygen on a para-xylene manufacturing process, the feed streams to the separation units (e.g., filter column) should be substantially free from molecular oxygen. As used herein, a stream is substantially free from molecular oxygen if it does not contain an amount of molecular oxygen (e.g., dissolved $O_2$ in a liquid stream, gaseous $O_2$ in a gas stream) that, if transferred to the filtrate (specifically to the liquid secondary component of the filtrate), would adversely affect the performance of a downstream unit operation (e.g., isomerization unit or heat exchanger disposed between the isomerization and separation units). For example, each of the filter column feed streams preferably contains about 5 parts per million (ppm) by weight or less (more preferably about 2 ppm or less, and even more preferably about 1 ppm or less) molecular oxygen, based on the total weight of the stream, and an individual stream can be simply free from molecular oxygen. Accordingly, the molecular oxygen concentration of the liquid secondary component of the filter column filtrate is less than that of the feed, and preferably is about 2 ppm by weight or less (more preferably about 0.7 ppm by weight or less, and even more preferably about 0.4 ppm by weight or less), based on the total weight of the filter column filtrate.

The use of filter columns, in accordance with the processing conditions set forth herein, further improves process efficiencies related to both product component recovery and operating costs. For example, in a crystallization/reslurry process using filter columns to purify and recover para-xylene, yield can be increased while simultaneously reducing operating costs related to crystallization refrigeration duty and isomerization recycle.

Additional embodiments of the process are also disclosed herein. For example, in one such embodiment, a process for purifying a solid product from slurry feed includes feeding a slurry and a displacement fluid to a filter column. The slurry includes product component solids and a liquid secondary component, and both the slurry and displacement fluid are substantially free of molecular oxygen. The filter column at least partially separates the product component solids and the liquid secondary component of the slurry to form a filtrate (including the liquid secondary component and at least a portion of the displacement fluid) and a filter cake (including the product component solids), such that the molecular oxygen concentration of the filtrate is less than or equal to the molecular oxygen concentration of the slurry. Preferably, the molecular oxygen concentration of the filtrate is about 2 ppm by weight or less, more preferably 0.7 ppm by weight or less, and even more preferably about 0.4 ppm by weight or less. Preferably, the displacement fluid is substantially free of molecular oxygen, and includes a gas and/or a liquid, both of which are non-reactive with the product component crystals, for example including nitrogen (most preferred), carbon dioxide, hydrogen, methane, ethane, natural gas, helium, xenon, argon, neon, and combinations thereof. Optional process steps include feeding a flush fluid to the filter column (where the flush fluid also is substantially free of molecular oxygen) and/or converting at least a portion of the liquid secondary component of the filtrate to liquid-phase product component in a downstream chemical reactor.

In another embodiment, a process for crystallizing a product includes first crystallizing a liquid feed stream including a liquid secondary component and a liquid product component having a melting point higher than that of the liquid secondary component. The liquid feed stream is crystallized in a crystallizer operating at a temperature sufficient to crystallize at least a portion of the liquid product component to form a slurry effluent including product component crystals and the liquid secondary component. The product component crystals and the liquid secondary component of the slurry effluent are then at least partially separated in a filter column to form a filtrate that includes the liquid secondary component, and a filter cake that includes the product component crystals. At least a portion of the liquid secondary component in the filtrate is then converted to the liquid product component.

In yet another embodiment, a process for reslurrying an at least partially crystallized product includes a reslurry stage process that includes at least partially separating (preferably in a filter column) product component crystals, present in a liquid product component, and a liquid secondary component, the liquid product and liquid secondary components present in a slurry feed, wherein the product component crystals have a melting point higher than that of the liquid secondary component to form a filtrate (including the liquid secondary component) and an enriched product stream (including the product component crystals). Both the enriched product stream and a reslurry diluent (including the liquid product component and the liquid secondary component) are fed to (combined in) a reslurry drum containing product component crystals. The product component crystals are then equilibrated with the liquid product and liquid secondary components in the reslurry drum for a time sufficient to form a reslurry effluent including both the product component crystals and the liquid secondary component.

In another embodiment, a process for the production of a crystallized product includes performing two or more crystallization stage processes in series, wherein each crystallization stage process includes first crystallizing a liquid feed stream containing a liquid secondary component and a liquid product component having a melting point higher than that of the liquid secondary component. The liquid feed stream is crystallized in a crystallizer operating at a temperature sufficient to crystallize at least a portion of the liquid product component to form a slurry effluent including product component crystals and the liquid secondary component. The product component crystals and the liquid secondary component of the slurry effluent are then at least partially separated in a filter column, wash column, or centrifuge (although at least one filter column is used) to form a filtrate including the liquid product component and the liquid secondary component, and an enriched product stream including the product component crystals. The liquid feed stream for each crystallization stage other than the first crystallization stage includes the filtrate from the preceding, upstream crystallization stage.

In still another embodiment, a process for recovering a solid product from a centrifuge filtrate includes first at least partially separating a slurry feed stream including a liquid and dispersed solids in a centrifuge to form at least a high-solids filtrate and a centrifuge cake. The high-solids filtrate contains the liquid and the dispersed solids, wherein the weight concentration of the dispersed solids in the high-solids filtrate is about 5 wt. % to about 50 wt. %, based on the total weight of the high-solids filtrate, and the centrifuge cake contains the liquid and the dispersed solids, wherein the weight concentration of the dispersed solids in the centrifuge cake is more than 50 wt. %, based on the total weight of the centrifuge cake. The dispersed solids and the liquid in the high-solids filtrate are then at least partially separated in a filter column to form a filter column filtrate including the liquid and a filter column cake including the dispersed solids, wherein the filter column cake has a weight concentration of the dispersed solids greater than that of the filter column filtrate.

Any of the above-described embodiments can be used to separate and purify para-xylene (which can be crystallized into solid form) from a mixture of $C_8$ aromatic hydrocarbons, including ortho-xylene, meta-xylene, and/or ethylbenzene. As evident from the foregoing summary, the disclosed process is not simply limited to purification of para-xylene from a mixture of xylene isomers; but, also is applicable to any solids-liquids separation process where molecular oxygen is considered an undesired process contaminant.

Additional features of the invention may become apparent to those skilled in the art from a review of the following detailed description, taken in conjunction with the drawings, examples, and appended claims.

BRIEF DESCRIPTION OF THE DRAWINGS

For a more complete understanding of the disclosure, reference should be made to the following detailed description and accompanying drawings wherein.

While the disclosed processes are susceptible of embodiments in various forms, specific embodiments of the invention are illustrated in the drawings (and will hereafter be described) with the understanding that the disclosure is intended to be illustrative, and is not intended to limit the invention to the specific embodiments described and illustrated herein.

DETAILED DESCRIPTION OF THE INVENTION

Generally disclosed herein are processes capable of separating solids from a solid-liquid slurry under conditions that desirably prevent ingress of molecular oxygen into the process, wherein the presence of molecular oxygen ($O_2$) may deleteriously affect process efficiencies, safety, and/or product yields. Accordingly, in an exemplary general embodiment of the inventive process, para-xylene and molecular oxygen are separated from a slurry containing the same and other xylene isomers under conditions that prevent ingress of molecular oxygen into the process. The para-xylene and molecular oxygen preferably are separated from the slurry in a filter column, under conditions that prevent ingress of molecular oxygen into the process, to produce a filter cake containing para-xylene, and to produce a filtrate containing a liquid product component, the liquid product component including a para-xylene lean product.

In another exemplary general embodiment, the process is a separation process that includes purifying para-xylene from a slurry containing the same and other xylene isomers under conditions that prevent ingress of molecular oxygen into the separation process, to produce a para-xylene lean product, and isomerizing the para-xylene lean product of the separation. The para-xylene preferably is purified from the slurry in a filter column, under conditions that prevent ingress of molecular oxygen into the separation process, to produce a filter cake containing para-xylene and a filtrate containing a liquid product component, the liquid product component including the para-xylene lean product.

In accordance with these exemplary general embodiments, the filtrate may further include a displacement fluid. Preferably, at least one of the filter cake and filtrate displacement fluid includes at least a portion of the molecular oxygen introduced to the process. As used herein, "at least a portion of the molecular oxygen introduced to the process" means at least about 40%, preferably at least about 45%, and more preferably at least about 50% of the molecular oxygen introduced to the process. Furthermore, at least one of the filter cake and filtrate displacement fluid preferably includes substantially all of the molecular oxygen introduced to the process. As used herein, "substantially all of the molecular oxygen introduced to the process" means at least about 80%, preferably at least about 90%, and more preferably at least about 95% of the molecular oxygen introduced to the process.

Among the various other embodiments disclosed herein are processes involving the use of filter columns to separate solids from a solid-liquid slurry, for example in melt crystallization purification processes, under conditions specified to ensure that molecular oxygen does not infiltrate process streams. The processes utilize several unit operations generally described below. One such embodiment includes the operation of a filter column in a manner that limits the ingress of molecular oxygen into the filter column filtrate. Another embodiment of the disclosure includes the use of filter columns in combination with a crystallization/reslurry process, with particular embodiments being directed to sub-combinations including a crystallizer and a filter column or a reslurry drum and a filter column. An additional embodiment includes the use of filter columns in combination with a series arrangement of crystallizers. Another embodiment includes the use of a filter column in combination with a centrifuge to recover residual solids passing through the centrifuge into the centrifuge filtrate. Test and simulation data indicate that processes using filter columns according to the disclosure are effective at limiting the ingress of molecular oxygen into the process and further improve process efficiency.

One preferred embodiment of the disclosure includes a process for purifying a solid product from slurry feed under processing conditions that reduce or prevent molecular oxygen ingress into process flow streams (e.g., one or more streams exiting unit operations responsible for purifying the solid product). As an example of this embodiment, the process may include first feeding a solid/liquid slurry containing the components to be separated, a displacement fluid, and, optionally, a flush fluid to a filter column, all three of which flow streams are substantially free of molecular oxygen.

The solid/liquid slurry feed includes product component solids to be separated/recovered by the filter column and a liquid secondary component to be removed from the slurry feed. The disclosed purification process is suitable for the separation of any product component solids dispersed in a slurry with any liquid secondary component. When the purification process is performed in connection with a crystallization and/or reslurry step, the two components to be separated have a melting point difference, and the product component solids can be product component crystals formed in an upstream crystallization/reslurry step via crystallization of a liquid-phase product component. In a preferred embodiment, the disclosed processes (including those described below) are used to separate and purify para-xylene from other hydrocarbons, and the product component (whether in liquid or solid/crystalline form) therefore preferably includes para-xylene. Similarly, the liquid secondary component preferably includes ortho-xylene, meta-xylene, and/or ethylbenzene. As used herein, the liquid secondary component is referenced in the singular "component," but can refer to either a single chemical compound or a collection of chemical compounds that can be separated from a particular product component using the disclosed processes A filter column is a solid-liquid separation apparatus for concentrating a suspension. Examples of suitable filter columns are disclosed in U.S. patent application publication Nos. 2005/0056599 and 2007/0225539, the disclosures of which are hereby incorporated herein by reference. A suitable filter column includes a hollow cylinder containing one or more tubes having a specified outer diameter and extending in an axial direction within the hollow cylinder. The wall of each tube includes at least one filter that forms the only direct connection between the interior of the tube and the interior of the hollow cylinder. The filter column separates solids from liquids in a solid-liquid suspension (e.g., a solid product component suspended in a mother liquor) by directing the suspension into a first end of the filter column. A displacement fluid (e.g., a gas or liquid immiscible with the suspension liquid) applies a back-pressure to the second end of the filter column, helping to drive a portion of the suspension liquid through the filter into the tube interior to be withdrawn as a filtrate (e.g., mother liquor) from the filter column tubes, thereby forming a concentrated suspension (i.e., bed) of solids in the hollow cylinder and around the tubes. The concentrated suspension of solids is withdrawn from the second end of the filter column via a product overflow chute, for example in the form of a concentrated product cake containing small amounts of suspension liquid (e.g., mother liquor) and/or displacement fluid.

Optionally, a flush fluid is fed to the product chute to clear the product chute of obstructions. Preferably, when using a flush fluid, the product chute also includes a reslurry zone reservoir, for example when the flush fluid includes recycled suspension liquid (mother liquor) and/or liquid product component. In this reslurry embodiment of the filter column, the reslurry zone reservoir performs the function of a separate reslurry drum (see below). Analogous to the reslurry drum, a slurry effluent having product component crystals dispersed in a liquid including the liquid secondary component and a portion of the non-crystallized liquid product component exits the reslurry filter column through an outlet at the first end of the reslurry filter column. The use of a filter column incorporating a reslurry zone reservoir is a preferred configuration because it is compact, reducing the number of pieces of process equipment and further allowing the unit to be placed on-grade (i.e., in contrast to a centrifuge which relies on gravity to transport its filter cake and must be elevated). As used herein, the term "filter column" refers to both the general embodiment described above as well as the embodiment further including a reslurry zone reservoir and flush fluid.

In general, the displacement fluid can include a gas and/or a liquid, each of which preferably is inert, immiscible, and/or insoluble with respect to the product component (e.g., the product component solids/crystals are not soluble in the displacement fluid and the liquid product/secondary components are not miscible with the displacement fluid). When the product component includes para-xylene, the displacement fluid is substantially free of molecular oxygen (e.g., dissolved $O_2$ in a liquid displacement fluid, gaseous $O_2$ in a gaseous displacement fluid). When the product component includes para-xylene, then the displacement fluid preferably is a gas selected from the group consisting of nitrogen, carbon dioxide, hydrogen, methane, ethane, natural gas, one or more noble gases (e.g., helium, xenon, argon, neon), and mixtures thereof. Nitrogen is a particularly preferred displacement fluid. Nitrogen gas is effective to strip out any oxygen present in the feed and desirably ensure that the filtrate contains less oxygen than that in the feed. To the extent that the nitrogen gas is recycled, the oxygen present in this recycle stream can be removed prior to reusing the recycled nitrogen gas; however, there would be additional costs associated with this procedure.

Once the slurry feed, displacement fluid, and (optional) flush fluid are introduced into the filter column, the product component solids and the liquid secondary component of the slurry are separated in the filter column to form a filtrate and a filter cake. The filtrate contains the liquid secondary component and the displacement fluid, and it may further contain a low, residual amount of product component (e.g., liquid product component originally in the slurry feed, and/or fine product component solids able to pass through the filter column filter). The filter cake is predominantly composed of the product component solids, but will generally also contain a residual portion of the liquid secondary component that does not pass through the filter into the filtrate. In a para-xylene purification process, the filter cake generally has a cake wetness of about 15 wt. % to about 20 wt. %, meaning that the filter cake contains about 80 wt. % to about 85 wt. % solid para-xylene crystals and about 15 wt. % to about 20 wt. % mixed $C_8$ hydrocarbons in liquid form.

It has been found that the operation of a filter column in this manner can provide a process advantage related to the absence of (or prevention of the introduction of) molecular oxygen in the process flow streams (e.g., the filter column filtrate). It has been found that a filter column operated in accordance with the process conditions disclosed herein minimizes the molecular oxygen content of the filtrate to help prevent undesirable coking and plugging in the isomerization unit (reactor). Unlike other solid-liquid separators (e.g., some centrifuges), the filter column operated in accordance with the process conditions set forth herein ensures that the molecular oxygen concentration of the filtrate is less than or equal to the molecular oxygen concentration of the slurry feed. Accordingly, the filter columns should be operated at least at ambient pressure, and preferably at pressures exceeding ambient pressure (e.g., about 2 psig to about 30 psig), to minimize the molecular oxygen content of the filtrate. In highly preferable operation, the filter column is operated at an elevated pressure of at least about 0.5 psi in excess of ambient pressure (i.e., at least about 0.5 psig), even more preferably at least about 1.5 psi in excess of ambient pressure, still more preferably at least about 3 psi in excess of ambient pressure, even more preferably at least about 5 psi in excess of ambient pressure, still more preferably at least about 10 psi in excess of ambient pressure, and further more preferably at least about 15 psi in excess of ambient pressure. A highly preferred pressure range for operating the filter column is about 1.5 psi to about 3 psi in excess of ambient pressure (i.e., about 0.5 psig to about 3 psig). While a pressure exceeding ambient pressure is a condition necessary to ensuring no molecular oxygen ingress, a pressure too far in excess of ambient pressure will unnecessarily drive operating expenses of the process to a level where the economic benefits of the process may be lost. Furthermore, the vessel used to perform the separation will have a not-to-exceed pressure rating that effectively sets an upper limit on the operable pressure, which, in most cases will not be approached, though is nevertheless suitable. Consequently, close observation of the pressure should be maintained to enjoy the many benefits made possible by the findings presented herein.

Reference herein to a separating step operating pressure (or to the filter column pressures described in the preceding paragraph) refers to the lowest of multiple pressures under which the various portions (interior, feed inlets, and outlets) of a separation unit may operate. For example, where the separation unit is a filter column, it is understood that the column is not isobaric and that its practical operation is based on pressure gradients. Pressure is typically measured in the column in three locations to infer the gradients. A slurry feed pressure is the highest pressure of the three. The second highest of the three pressures is the displacement fluid inlet pressure. The lowest of the three pressures is the pressure at which the displacement fluid and filtrate exit the column. The pressure at any location within the column is bounded by the highest and lowest of these pressures. Accordingly, as long as the pressure at which the displacement fluid and filtrate exit the column is higher than atmospheric (ambient) pressure, then the pressure anywhere else within the column may be considered to be higher than atmospheric (ambient) pressure. Furthermore, as long as the pressure in the column (separation unit) exceeds atmospheric (ambient) pressure, molecular oxygen ingress can be prevented.

Generally, the amount of molecular oxygen present in the product-lean (e.g., para-xylene-lean) stream exiting the separation unit is related to the amount of such oxygen entering the unit through the feed and stripped in the unit by the displacement fluid. The feed streams to the filter column should be substantially free from molecular oxygen. In accordance with the process conditions disclosed herein, the filter column is operated at a pressure exceeding ambient pressure, and has no moving parts. As used herein, a stream is substantially free from molecular oxygen if it does not contain an amount of molecular oxygen (e.g., dissolved $O_2$ in a liquid stream, gaseous $O_2$ in a gas stream) that, if transferred to the filtrate (specifically to the liquid secondary component thereof), would adversely affect the performance of a downstream unit operation (e.g., isomerization unit or heat exchanger disposed between the isomerization and separation units). For example, each of the filter column feed streams preferably contains about 5 parts per million (ppm) by weight or less (more preferably about 2 ppm or less, and even more preferably about 1 ppm or less) molecular oxygen, based on the total weight of the stream, and an individual stream can be simply free from molecular oxygen. Operated in this manner, the filter column will not allow molecular oxygen from the ambient air to infiltrate the unit operation and contaminate the process streams flowing therethrough. Accordingly, the molecular oxygen concentration of the filter column filtrate preferably is about 2 ppm by weight or less (more preferably about 0.7 ppm by weight or less, and even more preferably about 0.4 ppm by weight or less), based on the total weight of the filter column filtrate.

As previously noted herein, the low level of molecular oxygen is particularly beneficial when the filtrate (specifically to the liquid secondary component thereof) is fed to a chemical reactor to convert liquid secondary component to product component, for example in a catalytic isomerization unit that converts ortho-xylene, meta-xylene, and ethylbenzene into para-xylene. (described in more detail below). Molecular oxygen in the isomerization unit feed is a contaminant, causing coking and plugging of the catalytic reactor and/or the preheater of the reactor. See, e.g., W. T. Koetsier and J. van Leenen, "Oxygen Induced Fouling in a Xylene Isomerization Reactor Bed," *Catalyst Deactivation*, 1987 (G. Delmon and G. F. Froment, eds.).

Figure 1:
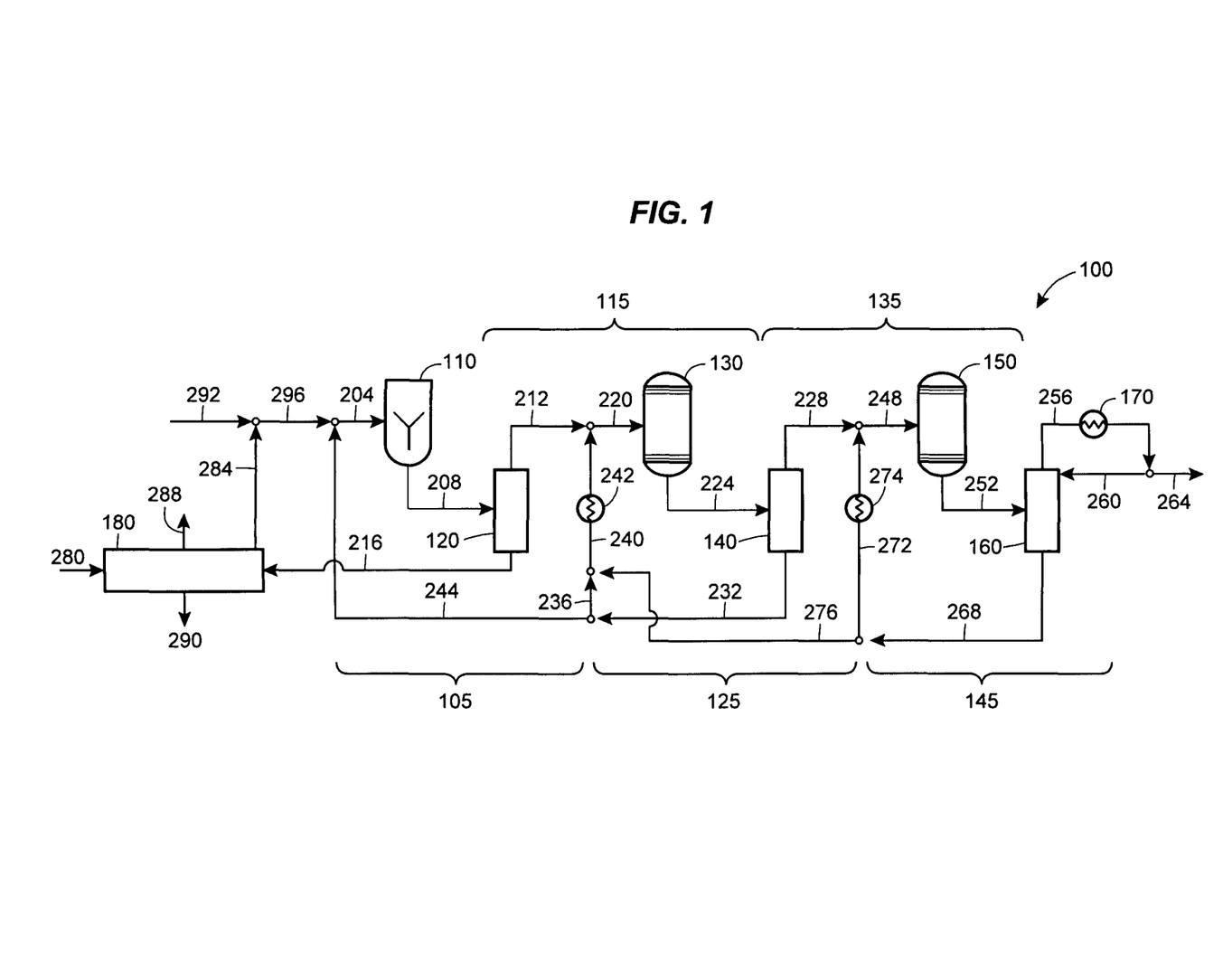
FIG. 1 is a process flow diagram illustrating a crystallization/reslurry process using two reslurry stages and filter columns to recover a solid (crystalline) product component.

FIG. 1 illustrates a crystallization/reslurry process 100 using a crystallization stage 105 followed by a first reslurry stage 125 and a second reslurry stage 145 in connection with at least one filter column to recover a solid (crystalline) product component from a liquid multi-component feed, which solid product component can be subsequently melted to form a substantially pure liquid product component. The crystallization stage 105 includes a crystallizer 110 and a separation unit 120. The crystallization stage 105 is followed by the first reslurry stage 125, which includes a reslurry drum 130 and a separation unit 140. The first reslurry stage 125 is followed by the second (or "product" or "final") reslurry stage 145, which includes a reslurry drum 150 and a separation unit 160.

Equivalently, the crystallization/reslurry process 100 can be viewed as a series of one or more separation/reslurry stages preceded by the crystallizer 110 (which feeds the first separation/reslurry stage) and followed by the separation unit 160 (which purifies the product effluent from the final separation/reslurry stage). This is illustrated in FIG. 1 by two separation/reslurry stages 115 and 135, although the general crystallization reslurry process 100 could have only a single separation/reslurry stage, or more than two separation/reslurry stages. The separation/reslurry stage 115 includes the separation unit 120 and the reslurry drum 130, and is followed in series by the separation/reslurry stage 135, which includes the separation unit 140 and the reslurry drum 150.

A crystallization vessel (crystallizer) cools an upstream liquid feed having at least two miscible components to recover one of the liquid feed components. A suitable example of a melt crystallization purification process is disclosed in U.S. Pat. No. 3,177,265, the disclosure of which is hereby incorporated herein by reference. The liquid feed includes a liquid product component to be separated from the feed and a liquid secondary component that is desirably not recovered with the liquid product component, and is fed to the inlet of the crystallizer. The liquid product component has a melting point higher than the melting point of the liquid secondary component. The crystallizer cools the liquid feed stream to a temperature sufficient to crystallize at least a portion the liquid product component. For a particular liquid feed, the temperature can be limited by the eutectic temperature of the feed system. Thus, the crystallizer preferably operates at a temperature above the eutectic temperature defined by the mixture of the product and secondary components to avoid the co-crystallization of the secondary component along with the product component. The crystallizer preferably has a sufficient volume/residence time to crystallize a substantial portion of the liquid product component in the liquid feed. A slurry (i.e., solid-liquid suspension) effluent exits the crystallizer through an outlet. The slurry effluent has substantially pure product component crystals dispersed in a liquid that primarily includes the liquid secondary component, but also possibly includes a portion of the non-crystallized liquid product component.

A reslurry drum equilibrates an upstream filter cake of product component crystals with a usually warmer diluent stream containing an additional (liquid) product component to provide a slurry suitable for downstream processing. A suitable reslurry drum is described in U.S. Pat. No. 6,565,653, the disclosure of which is hereby incorporated herein by reference. A solid cake of product component crystals and a liquid diluent containing both the liquid product and secondary components are fed to an inlet of a suitable reslurry drum. The solid cake and liquid diluent can be added to the reslurry drum separately (i.e., via two different feed lines), or they can be mixed upstream of the reslurry drum and added thereto via a single feed line. The reslurry drum is a reservoir containing product component crystals, and has sufficient volume/residence time to equilibrate the product component crystals with the liquid product component in the reservoir. The reslurry drum contents are preferably agitated while equilibrating. A slurry (i.e., solid-liquid suspension) effluent exits the reslurry drum through an outlet. The slurry effluent has product component crystals dispersed in a liquid including the liquid secondary component and a portion of the non-crystallized liquid product component.

In general, an individual separation unit can be a filter column, a wash column, or a centrifuge (described herein), or any other type of solid-liquid separator known in the art. In embodiments according to the disclosure, at least one of the separation units is a filter column, and the filter column preferably is used in at least one non-product (or non-final) reslurry stage. For example, in the embodiment illustrated in FIG. 1, at least one of the separation units 120, 140, and 160 is a filter column, and the filter column preferably is used as either or both of the separation units 120 and 140. In contrast, the separation unit 160 preferably is a non-filter column, for example a wash column or a centrifuge.

Filter columns are preferred upstream (i.e., non-product stage) separation units based on a variety of process efficiencies they impart. For example, relative to centrifuges, filter columns have no rotating parts (thus simplifying construction and maintenance), they impart less mechanical energy to process fluids (thus reducing refrigeration costs and product loss due to melting product crystals in a centrifuge cake), and they have higher recoveries than centrifuges based on a lower solids content in the filtrate. Additionally, filter columns allow filter cake wetness to be readily adjusted by varying the amount of displacement fluid, and they can be used to create more spatially compact processes and/or to increase the capacity of existing processes by replacing centrifuges with filter columns. Also, it has been found that under certain operating conditions disclosed herein, filter columns eliminate oxygen ingress into the process streams. Relative to wash columns, the absence of rotating parts is also an advantage, because wash columns generally either have rotating parts or omit rotating parts at the cost of a relatively low throughput per unit volume of the wash column. In addition, filter columns will have higher throughput at comparable conditions and will operate over a wider temperature range than wash columns.

In contrast, non-filter columns are preferred for use as separation units in product stages of the process. Typically, wash columns and centrifuges provide higher purity product streams relative to filter columns, and the product streams thus require less additional processing prior to downstream storage or use. While a filter column generally recovers a larger fraction of the product component crystals entering the separation unit in its product stream, the filter column also typically recovers a larger portion of the liquid secondary component in its product stream.

A wash column (or a hydraulic wash column) is a solid-liquid separation apparatus for concentrating a suspension. Examples of suitable wash columns are disclosed in U.S. Pat. Nos. 4,734,102 and 4,735,781, the disclosures of which are hereby incorporated herein by reference. A wash column includes a hollow cylinder containing one or more tubes having a specified outer diameter and extending in an axial direction within the hollow cylinder. The wall of each tube includes at least one filter that forms the only direct connection between the interior of the tube and the interior of the hollow cylinder. The wash column separates solids from liquids in a solid-liquid suspension (e.g., a solid product component suspended in a mother liquor) by directing the suspension into a first end of the wash column and a wash liquid into a second end of the wash column in countercurrent flow to the suspension, thereby forming a bed in the hollow cylinder and around the tubes. A filtrate (e.g., mother liquor) from the suspension escapes through the filters of the filter tubes into the interior of the tubes, and is then withdrawn from the wash column (e.g., from the first end of the wash column). A concentrated suspension of product component solids is withdrawn from the second end of the wash column. The wash liquid introduced at the second end of the wash column reslurries the concentrated suspension of solids and can melt some of the recovered solids. When the wash column is used to separate/purify a suspension derived from a melt crystallization process, the wash liquid includes molten crystal product from the suspension.

Centrifuges that are suitable for use as solid-liquid separators are not particularly limited and include those generally known in the art, such as, for example, filtering centrifuges, and in particular screen-bowl, solid-bowl, and/or pusher centrifuges. A suitable centrifuge generally includes an inlet for a solid-liquid suspension (e.g., a solid product component suspended in a mother liquor) to be separated, a first outlet for the concentrated solid suspension (e.g., product filter cake), and a second outlet for the filtered liquid (e.g., mother liquor) from the inlet suspension. In some embodiments (e.g., when a screen-bowl centrifuge is used), the centrifuge includes a third outlet for filtered liquid from the inlet suspension, with the second and third outlet streams differing in the relative amount of solids (e.g., residual, un-recovered product component) contained in each. In such embodiments, the second outlet can be a low-solids filtrate stream and the third outlet can be a high-solids filtrate stream.

In the embodiment illustrated in FIG. 1, the product component purification and recovery process begins by feeding a liquid feed stream 204 to the crystallizer 110. As described above, the feed stream 204 includes a liquid product component and a liquid secondary component, with the liquid product component having a melting point higher than that of the liquid secondary component. While the feed stream 204 generally can have any desired distribution between the liquid product secondary components, a preferred feed stream 204 for the purification of para-xylene includes about 10 wt. % to about 30 wt. % (more preferably about 15 wt. % to about 25 wt. %) of para-xylene. The crystallizer 110 operates at a temperature sufficient to crystallize at least a portion of the liquid product component from the liquid feed stream 204 to form a slurry effluent 208, which includes both product component crystals and the liquid secondary component. For example, when the feed stream 204 includes about 22 wt. % to about 23 wt. % para-xylene, a suitable crystallization temperature at atmospheric pressure is about −89° F. (−67° C.), or about 2° F. (1.1° C.) warmer than the binary eutectic temperature of about −91° F. (−68° C.). The crystallization temperature generally will vary based upon the amount of para-xylene present in any streams recycled to the feed stream 204. In a continuous para-xylene purification process, the residence time in the crystallizer 110 preferably is sufficient to crystallize a substantial portion of the liquid product component in the feed stream 204, for example at least about 50 wt. % (more preferably at least about 70 wt. %) of the liquid product component in the feed stream 204.

The slurry effluent 208 is then fed to the separation unit 120, which is a filter column in a preferred embodiment, but can also be a wash column or a centrifuge. The filter column 120 at least partially separates the product component crystals and the liquid secondary component of the slurry effluent 208 to form a filter cake 212 and a filtrate 216. The filter cake 212 is predominantly a solid cake of the product component crystals. Preferably, substantially all of the product component crystals from the slurry effluent 208 are recovered in the filter cake 212, and the filter cake 212 has a product component weight concentration (i.e., liquid and solids combined) greater than that of the filtrate 216. The filter cake 212 also includes a small amount of liquid, generally including both the liquid secondary component and the liquid product component. Specifically, the filter cake 212 preferably includes about 50 wt. % to about 99 wt. % (more preferably about 75 wt. % to about 88 wt. %) product component crystals, based on the total weight of the filter cake, including any liquids. The filtrate 216 is predominantly a liquid stream of the liquid secondary component, and preferably substantially all of the liquid secondary component from the slurry effluent 208 is recovered in the filtrate 216. However, the filtrate 216 can include a small amount of liquid product component and/or product component crystals. In general, the filtrate 216 can either be discarded as a reject stream or, preferably, recycled for further processing. The filter column 120 preferably includes an additional displacement fluid feed stream (not shown) to provide a driving force to displace the liquid product and secondary components from the slurry effluent 208 to form the filtrate 216.

The filter cake 212 and a reslurry diluent 240 are then fed to the first reslurry drum 130 via a stream 220. The reslurry diluent 240 is a liquid stream including both the liquid product component and the liquid secondary component. As illustrated in FIG. 1, the filter cake 212 and the reslurry diluent 240 are mixed upstream of the first reslurry drum 130 and then fed thereto via the single stream 220. In an alternate embodiment (not shown), however, the filter cake 212 and the reslurry diluent 240 can be fed to the first reslurry drum 130 as two separate streams.

In a further embodiment (not shown), the upstream separation unit 120 can be a centrifuge. In this case, the centrifuge effluent that is fed to the first reslurry drum 130 is similar to the filter cake 212 (i.e., a predominantly solid cake of the product component crystals with a small amount of the liquid secondary component and the liquid product component).

The reslurry drum 130 is a reservoir containing a solid-liquid slurry including the product component crystals, the liquid product component, and the liquid secondary component. In the reslurry drum 130, the product component crystals are equilibrated with the liquid product and secondary components for a time sufficient to form a reslurry effluent 224. The equilibration warms the reslurry effluent relative to the temperature of the filter cake 212. In a continuous process, the volume of the reslurry drum 130 and the feed rates of the filter cake 212 and the reslurry diluent 240 can be selected to provide a sufficient residence time for equilibration.

The reslurry effluent 224 is then fed to the separation unit 140, which operates analogously to the separation unit 120. The separation unit 140 can be a filter column, wash column, or centrifuge. Preferably, the separation unit 140 is a filter column. The filter column 140 operates similarly to the filter column 120, forming a filter cake 228 having contents analogous to the filter cake 212, and a filtrate 232, containing both the liquid product component and the liquid secondary component. While the filtrate 232 can be discarded as a reject stream, it is preferably recycled for further processing. As illustrated in FIG. 1, a portion 236 of the filtrate 232 is recycled to the reslurry drum 130 as the reslurry diluent 240 (in which case the filtrate 232 includes at least some liquid product component), and a portion 244 of the filtrate 232 is recycled to the crystallizer 110 as a contributor to the liquid feed stream 204. The reslurry diluent 240 can be heated with a diluent heater 242 providing a heat input selected such that the resulting temperature of the solid-liquid slurry in the reslurry drum 130 is adjusted to a desired value.

The filter cake 228 and a reslurry diluent 272 are then fed to the second reslurry drum 150 via a stream 248. The second reslurry drum 150 operates analogously to the first reslurry drum 130, thus forming a reslurry effluent 252 including the product component crystals, the liquid product component, and the liquid secondary component.

The reslurry effluent 252 is then fed to the final separation unit 160 in the illustrated embodiment of FIG. 1. The final separation unit 160 preferably is a solid-liquid separator other than a filter column, for example a wash column or a centrifuge. The separation unit 160 includes a filtrate 268 (similar to the other upstream filtrates 216 and 232) as a first output. The filtrate 268 is a liquid stream containing both liquid product component and liquid secondary component, although it can include a small amount of product component crystals. While the filtrate 268 can be discarded as a reject stream, it is preferably recycled for further processing. As illustrated in FIG. 1, a portion of the filtrate 268 is recycled to the second reslurry drum 150 as the reslurry diluent 272, and a portion 276 of the filtrate 268 is recycled to the first reslurry drum 130 as a contributor to the reslurry diluent 240. The reslurry diluent 272 can be heated with a diluent heater 274 providing a heat input selected such that the resulting temperature of the solid-liquid slurry in the reslurry drum 150 is adjusted to a desired value. The separation unit 160 also includes a product stream 256. The product stream 256 can include predominantly product component crystals along with some liquid product component (e.g., a washed filter cake formed when the separation unit 160 is a centrifuge), or it can include a substantial fraction of both the product component crystals and the liquid product component (e.g., a washed slurry output formed when the separation unit 160 is a wash column). A heater 170 preferably is used to melt any remaining product component crystals in the product stream 256. A portion of the melted product stream 256 preferably is recycled to the separation unit 160 as a wash liquid 260, and a portion is withdrawn as a final product stream 264 that is a purified liquid product component stream. Preferably, the wash liquid 260 and/or the final product stream 264 contains the liquid product component at a weight concentration of at least about 99.5 wt. % (preferably at least about 99.7 wt. %, more preferably least about 99.8 wt. %, for example about 99.9 wt. %).

The yield of the disclosed process can be increased by recycling the filtrate from the crystallization stage separation unit to a chemical reactor that can convert at least a portion of the liquid secondary component to the liquid product component, which can then be recycled to the crystallization stage 105. For example, when the disclosed processes are used to separate and purify para-xylene, the filtrate 216 from the separation unit 120 preferably is recycled to an isomerization unit 180 (i.e., a chemical reactor) to convert the liquid secondary component (i.e., ortho-xylene, meta-xylene, and/or ethylbenzene) to the liquid product component (i.e., para-xylene), thereby increasing the potential yield of the overall process 100. The isomerization unit 180 generally includes both a reactor for the catalytic conversion of ortho-xylene, meta-xylene, and/or ethylbenzene into para-xylene, and a distillation unit for the separation of a $C_8$-aromatic hydrocarbon product stream from heavier and lighter components. The details of the isomerization and distillation are known in the art, for example as described in U.S. Pat. No. 5,284,992, the disclosure of which is hereby incorporated herein by reference.

As illustrated in FIG. 1, a para-xylene-depleted (i.e., a para-xylene-lean) filtrate 216 (e.g., including up to about 15 wt. % para-xylene) and a hydrogen feed 280 are fed to the isomerization unit 180. The adjectives "para-xylene-depleted," "para-xylene-lean," and variations thereof when used in connection with describing a unit operation stream refer to a stream exiting a unit operation that contains less para-xylene than contained in a stream fed to that unit operation. The catalytic reaction in the isomerization unit 180 converts the inlet ortho-xylene, meta-xylene, and/or ethylbenzene into para-xylene, and also generates heavier and lighter hydrocarbon components. The reaction products are separated in the distillation portion of the isomerization unit 180 to form a light hydrocarbon waste stream 288 (e.g., including $C_1$ to $C_7$ aliphatic and aromatic hydrocarbons), a heavy hydrocarbon stream 290 (e.g., including $C_9$ and higher aliphatic and aromatic hydrocarbons), and an isomerate 284. The isomerate stream 284 generally includes the following mixture of $C_8$ aromatic hydrocarbons: about 20 wt. % to about 25 wt. % (e.g., about 22 wt. %) para-xylene, about 15 wt. % to about 30 wt. % ortho-xylene, about 40 wt. % to about 55 wt. % meta-xylene, and about 5 wt. % to about 15 wt. % ethylbenzene. As illustrated in FIG. 1, the isomerate stream 284 and a mixed xylene feed 292 are combined to form a crystallization stage feed 296. The crystallization stage feed 296 and the recycled portion 244 of the filtrate 232 are then combined to form the liquid feed stream 204 to the crystallizer 110.

Figure 2:
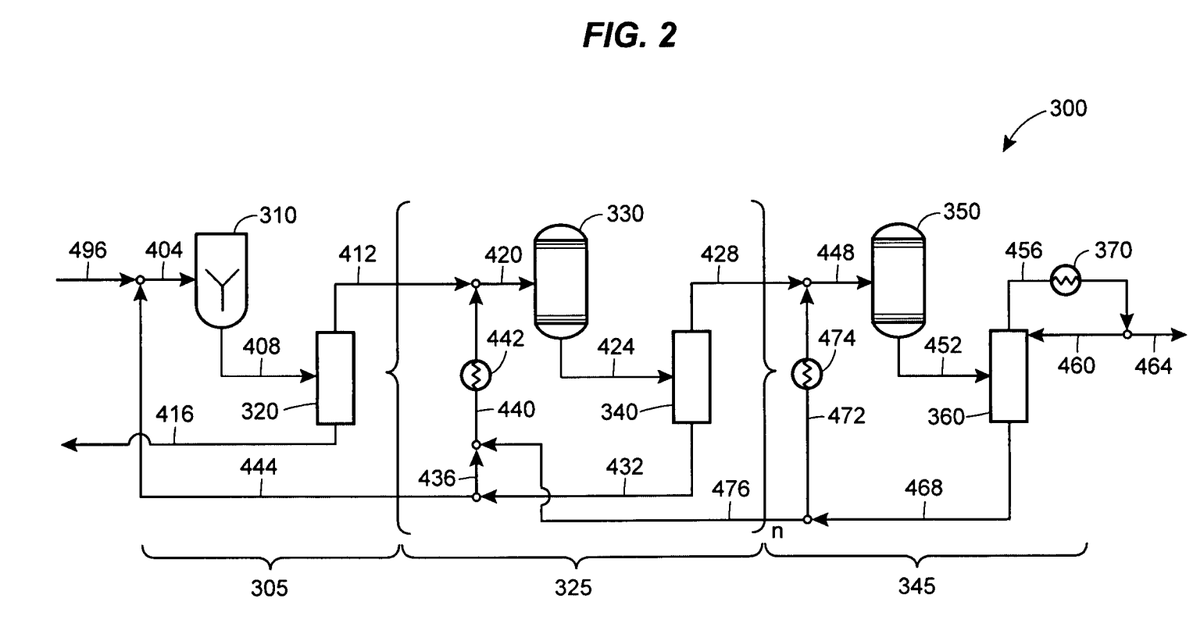
FIG. 2 is a process flow diagram illustrating a crystallization/reslurry process using an arbitrary number of reslurry stages and filter columns to recover a solid (crystalline) product component.

Although the described embodiment of the crystallization/reslurry process using filter columns illustrated in FIG. 1 includes a crystallization stage followed in series by two reslurry stages, the disclosed process is not limited thereto. FIG. 2 illustrates a generic crystallization/reslurry process using filter columns including a crystallization stage 305 followed in series by an arbitrary number n of intermediate reslurry stages 325 and a final reslurry stage 345. Any number of intermediate reslurry stages 325 is possible, including zero (i.e., $n \geq 0$, where n=0 represents a single reslurry process), such that the minimum number of purification/separation stages is two: the crystallization stage 305 followed by the final reslurry stage 345. One benefit of increasing the number of reslurry stages is that a given product purity can be obtained more energy-efficiently, or, alternatively, that a higher product purity can be obtained with an equivalent energy input. Other than the potential difference in the number of reslurry stages, like-numbered unit operations and streams in FIGS. 1 and 2 have analogous functions and are not described in any further detail.

For example, in the crystallization stage 305, the crystallizer 310 of FIG. 2 is analogous in function to the above-described crystallizer 110 of FIG. 1, having a feed stream 404 and a slurry effluent 408. The slurry effluent 408 is then fed to a separation unit 320 (preferably a filter column) that at least partially separates product component crystals and a liquid secondary component of the slurry effluent 408 to form a filter cake 412 and a filtrate 416.

As illustrated in FIG. 2, the reslurry feed stream for each reslurry stage $325_n$ includes the enriched product stream from the preceding, upstream purification or reslurry stage. This may more easily be visualized, as followed, by considering the process where n=3 and contemplating the various process steams in the middle of the three reslurry stages, i.e., reslurry stage $325_2$. In that middle reslurry stage $325_2$, a feed $420_2$ to a reslurry drum $330_2$ includes a contribution from an upstream filter cake $428_1$. In that middle reslurry stage $325_2$, a reslurry effluent $424_2$ is then fed to a separation unit $340_2$ (preferably a filter column) to form the downstream filter cake $428_2$ and a filtrate $432_2$. Considered more generically, a feed 420 to a reslurry drum 330 in an $n^{th}$ reslurry stage 325 includes a contribution from the upstream filter cake (i.e., filter cake 412 when n=1 and the enriched product stream is the crystallization stage 305 output, or upstream filter cake 428 when n≧2 and the enriched product stream is the $(n-1)^{th}$ reslurry stage 325 output). Within the $n^{th}$ reslurry stage 325, a reslurry effluent 424 is then fed to a separation unit 340 (preferably a filter column) to form a filter cake 428 and a filtrate 432. Preferably, the reslurry diluent for each reslurry stage includes a recycled portion of the reslurry stage filtrate from at least one of the same reslurry stage and a subsequent, downstream reslurry stage. Revisualizing again the process where n=3 and contemplating the various process steams in the middle of the three reslurry stages (i.e., reslurry stage $325_2$), a portion $436_2$ of the filtrate $432_2$ is recycled to the reslurry drum $330_2$ as a reslurry diluent $440_2$ (heated for example, by a reslurry heater $442_2$) in the middle reslurry stage $325_2$ A portion $444_2$ of the filtrate $432_2$ is recycled upstream to the reslurry drum $330_1$ of the first reslurry stage $325_1$. Considered more generically in the FIG. 2 illustration, a portion 436 of the filtrate 432 is recycled to the reslurry drum 330 as a reslurry diluent 440 (heated, for example, by a reslurry heater 442) in the $n^{th}$ reslurry stage 325, and a portion 444 of the filtrate 432 is recycled upstream, either to the crystallizer 310 (i.e., when n=1) or to the reslurry drum 330 of the $(n-1)^{th}$ reslurry stage 325 (i.e., via a stream 476 when n≧2).

In the final reslurry stage 345, the filter cake 428 from the preceding intermediate reslurry stage 325 and a reslurry diluent 472 are fed to a reslurry drum 350 via a stream 448. A reslurry effluent 452 from the reslurry drum 350 is then fed to a separation unit 360 (preferably a wash column or a centrifuge) to form a product stream 456 and a filtrate 468. Preferably, a portion of the filtrate 468 is recycled to the reslurry drum 350 as the reslurry diluent 472 (heated, for example, by a reslurry heater 474), and a portion 476 of the filtrate 468 is recycled upstream to the preceding intermediate reslurry stage 325 as a contributor to the reslurry diluent 440. A heater 370 preferably is used to melt any remaining product component crystals in the product stream 456. A portion of the melted product stream 456 preferably is recycled to the separation unit 360 as a wash liquid 460, and a portion is withdrawn as a final product stream 464 that is a purified liquid product component stream.

Figure 3:
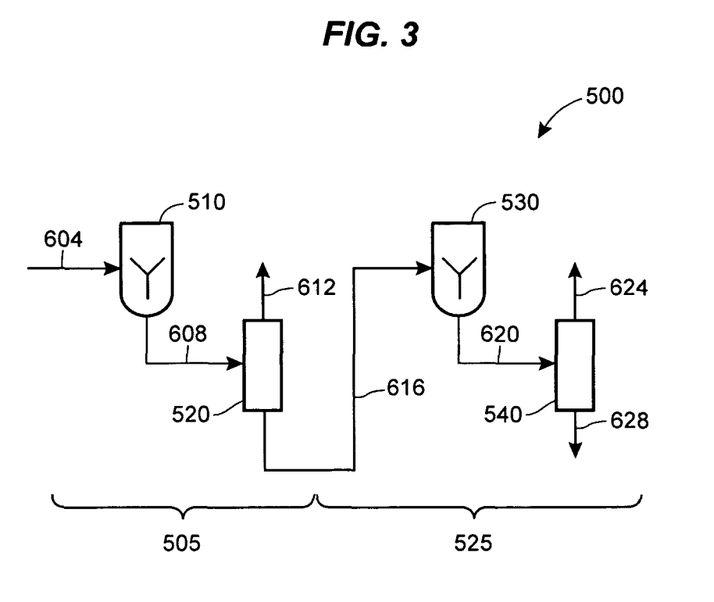
FIG. 3 is a process flow diagram illustrating a series arrangement of crystallizers and filter columns to recover a solid (crystalline) product component; and, FIG. 4 is a process flow diagram illustrating a series arrangement of a centrifuge and a filter column to recover a solid (crystalline) product component from a centrifuge filtrate.

FIG. 3 illustrates an additional embodiment of the disclosure, which includes a multistage crystallization process 500. The process 500 includes a series arrangement of at least two crystallization stages, for example a first crystallization stage 505 followed by a second crystallization stage 525 in connection with filter columns to recover a solid (crystalline) product component from a liquid multi-component feed (e.g., to separate and purify para-xylene from ortho-xylene, meta-xylene, and/or ethylbenzene). The first crystallization stage 505 includes a crystallizer 510 and a separation unit 520. Similarly, the second crystallization stage 525 includes a crystallizer 530 and a separation unit 540. At least one of the separation units 520 and 540 is a filter column. The other could be a filter column or it could be something other than a filter column, such as a wash column or a centrifuge.

Similar to the embodiment of FIG. 1, the product component purification and recovery process begins by feeding a liquid feed stream 604 to the crystallizer 510. The liquid feed stream 604 includes a liquid product component and a liquid secondary component, with the liquid product component having a melting point higher than that of the liquid secondary component. Similar to the crystallizer 110, the crystallizer 510 operates at a temperature sufficient to crystallize at least a portion of the liquid product component from the liquid feed stream 604 to form a slurry effluent 608 including both product component crystals and the liquid secondary component.

The slurry effluent 608 is then fed to the filter column 520 to at least partially separate the product component crystals and the liquid secondary component of the slurry effluent 608 to form a filter cake 612 and a filtrate 616. The filter cake 612 is predominantly a solid cake of the product component crystals. Preferably, substantially all of the product component crystals from the slurry effluent 608 are recovered in the filter cake 612, and the filter cake 612 has a weight concentration of the product component (i.e., including liquid and solids) greater than that of the filtrate 616. The filter cake 612 can be withdrawn from the process 500 as a product stream or further purified if desired. The filtrate 616 is predominantly a liquid stream of the liquid secondary component, and preferably substantially all of the liquid secondary component from the slurry effluent 608 is recovered in the filtrate 616. However, the filtrate 616 can include liquid product component and/or product component crystals.

In the second crystallization stage 525 (and any other subsequent crystallization stage), the liquid feed stream includes the filtrate from the preceding, upstream crystallization stage. Thus, as illustrated, the filtrate 616 is fed to the crystallizer 530 to form a slurry effluent 620 that is separated in the filter column 540 into a filter cake 624 and a filtrate 628.

The benefit of using a filter column in place of a centrifuge in the series arrangement of crystallizers (or in the crystallization/reslurry embodiments described above) is that the filter column adds significantly less energy (heat) to the filtrate than does the centrifuge. Specifically, the mechanical action of the centrifuge during separation imparts heat energy to the product component crystals, causing a portion of the crystals to melt, thereby reducing the recovered yield of the product component crystals in the centrifuge filter cake. In contrast, there is little to no heat generated during the normal operation of a filter column, thereby preventing the melt loss and improving the recovered yield of the product component crystals. Furthermore, and as explained in detail above, it has been found that certain separation steps (utilizing filter columns, for example), operated under conditions disclosed herein, in para-xylene manufacturing processes advantageously and desirably limit the ingress of molecular oxygen into various process streams.

Figure 4:
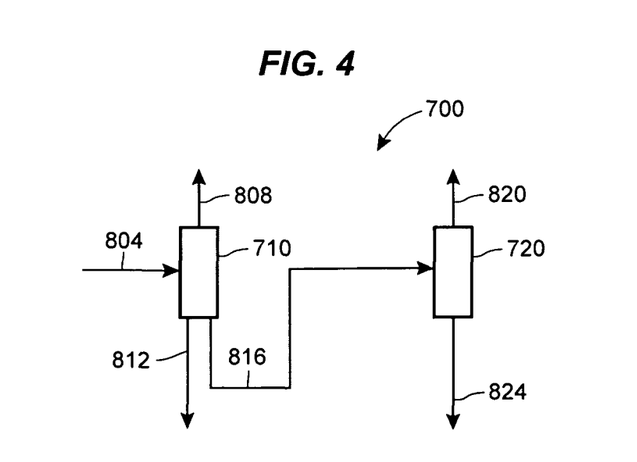

FIG. 4 illustrates yet an additional embodiment of the disclosure, which includes a multistage solid-liquid separation process 700. The process 700 includes an arrangement of a centrifuge 710 followed in series by a filter column 720. In this additional embodiment, the filter column 720 can increase the recovery of solids that might otherwise be lost in a centrifuge filtrate stream.

In FIG. 4, a slurry feed 804 including a liquid and dispersed solids is fed to the centrifuge 710 (e.g., a screen bowl centrifuge). The centrifuge 710 at least partially separates the components of the slurry feed 804, forming the following three output streams: a centrifuge cake 808 including the liquid and more than 50 wt. % of the dispersed solids, a low-solids filtrate 812 including about 5 wt. % or less of the dispersed solids, and a high-solids filtrate 816 including the liquid and about 5 wt. % to about 50 wt. % (e.g., at least about 10 wt. %) of the dispersed solids. The high-solids filtrate 816 is then fed to the filter column 720 to form a filter column cake 820 including the dispersed solids, and a filter column filtrate 824 including the liquid. The filter column cake 820 has a weight concentration of the dispersed solids greater than that of the filter column filtrate 824.

Generally, the centrifuge cake 808 and filter column cake 820 can be withdrawn as a product stream and passed along for further processing (e.g., purification, melting, storage). The low-solids filtrate 812 and the filter column filtrate 824 can be withdrawn as waste streams or processed further. For example, when the embodiment of FIG. 4 is applied to a process for the separation and purification of para-xylene (i.e., the dispersed solids are para-xylene crystals and the liquid is a mixture of $C_8$ hydrocarbons, including liquid para-xylene), the filtrates 812 and 824, which are relatively lean in para-xylene, can be sent to an isomerization unit to generate additional para-xylene and then recycled to a separation/purification process (e.g., as described above).

Subsumed in the disclosed process (and the various embodiments thereof) is an understanding by those skilled in the art of suitable processing equipment and controls necessary to carry out the process. Such processing equipment includes, but is not limited to, appropriate piping, valves, unit operations equipment (e.g., reactor vessels with appropriate inlets and outlets, heat exchangers, separation units, etc.), associated process control equipment, and quality control equipment. Furthermore, those skilled in the art should readily understand that major unit operations described herein, such as, for example in FIG. 1, the following may be carried out with like equipment in parallel: separation units 120, 140, and 160; heaters 170, 242, and 274; and, reslurry drums 130 and 150. Other processing equipment, especially where particularly preferred, is specified herein.

EXAMPLES

The following examples are provided to illustrate the invention, but are not intended to limit the scope thereof.

Example 1

Tests were conducted on the slurry feed and filtrate liquid secondary component outlet streams of different solid-liquid separators to measure the effect of the separators on the molecular oxygen content of the separator process streams. The oxygen measurements were made with an ORBISPHERE Model 2611E oxygen analyzer (available from Hach Ultra, Geneva, Switzerland), which was calibrated using air having a 20.9% oxygen content. Samples were warmed to 25° C. prior to oxygen measurement, and an enclosed sample system (i.e., completely isolated from atmospheric oxygen) was used in all tests.

A filter column using nitrogen as a displacement fluid and operating as a first-stage separation unit (i.e., analogous to the separation unit 120 in FIG. 1) in a para-xylene purification process was tested. The filter column slurry feed and filtrate were analyzed for molecular oxygen content over an approximate one-day period. Over the test period, the data (summarized in Table 1) indicate that there was no oxygen ingress into the filter column. The data indicate that the filter column stripped some of the oxygen that was present in the feed, so that the liquid secondary component of the filter column filtrate had a lower oxygen level than the feed. Specifically, the feed contained approximately 1.5 parts per million (ppm) by weight oxygen, while the filtrate liquid secondary component contained less than about 0.4 ppm oxygen. The relatively low oxygen content of the filtrate liquid secondary component makes the filtrate liquid secondary component particularly suitable for recycling to an isomerization unit for further para-xylene production. The filter column pressure measurements were recorded in units of pounds per square inch gauge (psig), thereby obviating the necessity of recording atmospheric/ambient pressure.

TABLE 1

Molecular Oxygen Content of Filter Column Streams and Filter Column Operating Pressures

| Measurement Time | $O_2$ in Filter Column (ppm) | | Filter Column Pressure (psig) | | |
|---|---|---|---|---|---|
| | Feed | Filtrate | Slurry Feed Inlet | Filtrate and $N_2$ Inlet | $N_2$ Outlet |
| 0.00 Hours | 1.84 | 0.38 | ~150 | ~50 | ~2.5 |
| 19.67 Hours | 1.41 | 0.30 | ~100 | ~40 | ~2 |
| 25.25 Hours | 1.37 | 0.30 | ~100 | ~55 | ~2 |

As a comparison, a conventional centrifuge operating as a first-stage separation unit (i.e., analogous to the separation unit 120 in FIG. 1) in a para-xylene purification process was also tested. The slurry feed and filtrate of two centrifuges were analyzed for molecular oxygen content. Conventional high-speed centrifuges allow oxygen ingress into the process, both in steady state operation and when they are periodically opened to the atmosphere for maintenance and repair. In contrast with the filter column, the data (summarized in Table 2) illustrate that oxygen is introduced by conventional centrifuges. Specifically, the oxygen content increases from 0.15 ppm in the centrifuge feed to more than about 0.7 ppm (e.g., about 0.8 ppm to about 1.5 ppm) in the centrifuge filtrate. Because the filtrate oxygen content is increased relative to that of the filter column, feeding the centrifuge filtrate to an isomerization unit for para-xylene production without further process steps to reduce the oxygen content could result in significant coking and/or plugging of the isomerization unit and its pre-heater.

TABLE 2

Molecular Oxygen Content of Centrifuge Streams

| Centrifuge # | $O_2$ in Centrifuge Feed (ppm) | $O_2$ in Centrifuge Filtrate (ppm) |
|---|---|---|
| 1 | 0.15 | 0.76 |
| 2 | 0.15 | 1.51 |

Example 2

A crystallization/double-reslurry process for the purification of para-xylene (i.e., as illustrated in FIG. 1) was simulated to compare the process efficiencies associated with the use of filter column separation units in place of centrifuges. Table 3 presents mass balance information for the process of FIG. 1 in which the separation units 120 and 140 are both filter columns, and the separation unit 160 is a wash column. Table 4 presents mass balance information for the process of FIG. 1 in which all separation units 120, 140, and 160 are centrifuges. In Tables 3 and 4, the "stream number" refers to the streams as labeled in FIG. 1. The "composition" entry includes the given component's contribution from any solid and/or liquid phase present in the stream. The "other $C_8$" composition entry includes ortho-xylene, meta-xylene, ethylbenzene, and any other residual aliphatic and aromatic hydrocarbons. Each process generally produces streams of increasing para-xylene purity at each stage outlet (up to, for example, a para-xylene purity of 99.9 wt. % in stream 264 in the filter column process) and produces a filtrate stream 216 relatively rich in meta-xylene, ortho-xylene, and ethylbenzene.

TABLE 3

Para-Xylene Purification Process Using Filter Columns

| | | Stream Number | | | |
|---|---|---|---|---|---|
| | | 296 | 216 | 264 | 292 |
| Temperature | (° F.) | 97.5 | 74.6 | 80.0 | |
| Flow Rate | (lb/hr) | | | | |
| | Net Stream | 710.9 | 610.9 | 100.0 | 130.4 |
| | p-Xylene | 148.6 | 48.9 | 99.9 | 23.2 |
| Composition | (wt. %) | | | | |
| | p-Xylene | 20.9 | 8.0 | 99.9 | 17.8 |
| | Other | 79.1 | 92.0 | 0.1 | 82.2 |

TABLE 4

Para-Xylene Purification Process Using Centrifuges

| | | Stream Number | | | |
|---|---|---|---|---|---|
| | | 296 | 216 | 264 | 292 |
| Temperature | (° F.) | 97.5 | 73.1 | 80.0 | |
| Flow Rate | (lb/hr) | | | | |
| | Net Stream | 732.3 | 632.3 | 100.0 | 130.7 |
| | p-Xylene | 153.1 | 53.1 | 99.85 | 23.3 |
| Composition | (wt. %) | | | | |
| | p-Xylene | 20.9 | 8.4 | 99.85 | 17.8 |
| | Other | 79.1 | 91.6 | 0.15 | 82.2 |

The values listed in Tables 3 and 4 were computed on a basis of 100 lb/hr para-xylene produced in the final product stream 264 based on material balance principles. The partitioning of feed streams to the various solid-liquid separation units 120, 140, and 160 can be (and was) determined based on a prescribed weight fraction of solids passing to the filter cake and filtrate for each separation unit. The formation of solids (i.e., due to crystallization of para-xylene) in the crystallizer 110 and the reslurry drums 130 and 150 is based on an assumption of thermal equilibrium.

Table 5 presents a comparison of global process properties between the filter column process (Table 3) and the centrifuge process (Table 4). As process efficiency parameters, "purity" refers to the concentration of para-xylene in the final product stream 264, "recovery" refers to the amount of para-xylene in the final product stream 264 relative to the amount of para-xylene in the crystallization stage feed 296, and the "yield" refers to the amount of para-xylene in the final product stream 264 relative to the amount of hydrocarbons in the mixed xylene feed 292. The "isomerization unit feed" refers to the total amount of hydrocarbons fed to isomerization unit 180 via the filtrate 216 per unit of para-xylene produced in the final product stream 264. The "crystallizer duty" indicates the cooling duty for the crystallizer unit operation. Both the "isomerization unit feed" and the "crystallizer duty" are dimensionless values, normalized by the feed/duty computed for the centrifuge case. The binary eutectic temperatures relevant for the compositions being fed to the crystallizer 110 are also indicated in Table 5.

TABLE 5

Comparison of Para-Xylene Purification Processes

| Process Parameter | | Filter Column | Centrifuge | % Difference |
|---|---|---|---|---|
| p-Xylene Efficiency | (wt. %) | | | |
| | p-Xylene Purity | 99.9 | 99.85 | |
| | p-Xylene Per-Pass Recovery | 67.2 | 65.2 | |
| | p-Xylene Yield | 76.6 | 76.4 | |
| Isomerization Unit Feed | (—) | 0.966 | 1.000 | −3.4% |
| Crystallizer Duty | (—) | 0.973 | 1.000 | −2.7% |
| Binary Eutectic | (° F.) | −90.9 | −90.9 | |

The data of Table 5 indicate the process advantages of using filter and wash columns in a para-xylene purification process in accordance with the process conditions disclosed herein, as compared to a similar process using conventional centrifuge solid-liquid separation technology. In general, the filter column process operated under the conditions disclosed herein (e.g., the filter column process) is more efficient, resulting in higher para-xylene final product purity, recovery, and yield. The filter column process also significantly reduces the duty imposed on the isomerization unit 180. The para-xylene concentration of the filtrate 216 is higher for the centrifuge process by 0.4 wt. % para-xylene, meaning that a larger fraction of the para-xylene is not recovered and is unnecessarily recycled in the centrifuge process (i.e., about 8.6% more para-xylene is recycled compared to the filter column process). This loss can be caused, for example, by the mechanical heat generated in a centrifuge that can melt some of the solid para-xylene crystallized in the crystallizer 110, resulting in a portion of para-xylene that is passed to the filtrate 216 instead of being recovered in the filter cake 212. A reduced flow rate of recycled material to the isomerization unit 180 when using filter columns (i.e., a 3.4% reduction), under the conditions disclosed herein, results in reduced operating costs for the isomerization unit 180. The filter column process is also more energy efficient, having a lower crystallizer refrigeration duty (i.e., a 2.7% reduction). These efficiencies outweigh any inefficiencies concomitant with the fact that a filter column generally produces a wetter product cake compared to a centrifuge.

Because other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Accordingly, the foregoing description is given for clearness of understanding only, and no unnecessary limitations should be understood therefrom, as modifications within the scope of the invention may be apparent to those having ordinary skill in the art.

Throughout the specification, where the compositions, processes, or apparatus are described as including components, steps, or materials, it is contemplated that the compositions, processes, or apparatus can also comprise, consist essentially of, or consist of, any combination of the recited components or materials, unless described otherwise. Combinations of components are contemplated to include homogeneous and/or heterogeneous mixtures, as would be understood by a person of ordinary skill in the art in view of the foregoing disclosure.

What is claimed is:

1. A process for crystallizing a product, the process comprising:
   (a) crystallizing a liquid feed stream, the feed stream comprising a liquid secondary component and a liquid product component having a melting point higher than that of the liquid secondary component, in a crystallizer operating at a temperature sufficient to crystallize at least a portion of the liquid product component to form a slurry effluent comprising product component crystals and the liquid secondary component;
   (b) at least partially separating the product component crystals and the liquid secondary component of the slurry effluent in a filter column to form
      (i) a filtrate comprising the liquid secondary component and
      (ii) a filter cake comprising the product component crystals;
   (c) converting at least a portion of the liquid secondary component of the filtrate to the liquid product component in a chemical reactor; and
   (d) performing at least one reslurrying process stage in series following the separation of (b), each of the least one reslurrying process stages comprising:
      (i) combining in a reslurry drum the product components crystals and an additional reslurry diluent comprising the liquid product component and the liquid secondary component; and,
      (ii) equilibrating the product component crystals with the liquid product and liquid secondary components in the reslurry drum for a time sufficient to form a reslurry effluent comprising the product component crystals and the liquid secondary component;
      (iii) at least partially separating the product component crystals and the liquid secondary component in a separation unit to form
         (A) a filtrate comprising the liquid secondary component; and
         (B) a filter cake comprising the product component crystals;
   wherein the separation unit in at least one of the least one reslurrying process stage comprises a filter column; and the separation unit in the last stage of the at least one reslurrying process stage is not a filter column.

2. The process of claim 1, wherein the filter cake comprises about 50 wt. % to about 99 wt. % product component crystals, based on the total weight of the filter cake.

3. The process of claim 1, wherein the liquid product component is para-xylene, and the liquid secondary component is selected from the group consisting of ortho-xylene, meta-xylene, ethylbenzene, and combinations thereof.

4. The process of claim 3, wherein the liquid feed stream comprises about 10 wt % to about 30 wt. % liquid product component, based on the total weight of the liquid feed stream.

5. The process of claim 3, wherein the chemical reactor comprises an isomerization reactor for converting at least one of orthoxylene, metaxylene, and ethylbenzene to paraxylene.

6. The process of claim 1, wherein: step (a) further comprises combining with the liquid feed stream a recycle stream comprising the liquid product component and the liquid secondary component, and the liquid feed stream has a weight concentration of the liquid product component less than that of the recycle stream.

7. The process of claim 1, wherein the filter cake has a product component weight concentration greater than that of the filtrate.

8. The method of claim 1, wherein the separation unit in the last stage of the at least one reslurrying process stage comprises a wash column.

9. The process of claim 8, wherein the liquid product component is paraxylene, and the liquid secondary component is selected from the group consisting of orthoxylene, metaxylene, ethylbenzene, and combinations thereof.

10. The process of claim 9, wherein the chemical reactor comprises an isomerization reactor for converting at least one of orthoxylene, metaxylene, and ethylbenzene to paraxylene.

11. A process for crystallizing a product, the process comprising:
   (a) crystallizing a liquid feed stream, the feed stream comprising a liquid secondary component and a liquid product component having a melting point higher than that of the liquid secondary component, in a crystallizer operating at a temperature sufficient to crystallize at least a portion of the liquid product component to form a slurry effluent comprising product component crystals and the liquid secondary component;
   (b) at least partially separating the product component crystals and the liquid secondary component of the slurry effluent in a filter column to form
      (i) a filtrate comprising the liquid secondary component and
      (ii) a filter cake comprising the product component crystals;
   (c) converting at least a portion of the liquid secondary component of the filtrate to the liquid product component in a chemical reaction; and
   at least one additional crystallization stage in series, wherein each at least one additional crystallization stage process comprises:
      (i) crystallizing a liquid feed stream, the feed stream comprising the liquid secondary component and the liquid product component,
      (ii) at least partially separating the product component crystals and the liquid secondary component of the slurry effluent in a separation unit
         (A) a filtrate comprising the liquid product component and the liquid secondary component and
         (B) an enriched product stream comprising the product component crystals; and
   wherein the separation unit in at least one of the least one additional crystallization stage comprises a filter column, and the last one of the least one additional crystallization stage is not a filter column.

12. The method of claim 11, wherein the separation unit in the last one of the least one additional crystallization stage comprises a wash column.

13. The process of claim 12, wherein the liquid product component is paraxylene, and the liquid secondary component is selected from the group consisting of orthoxylene, metaxylene, ethylbenzene, and combinations thereof.

14. The process of claim 13, wherein the chemical reactor comprises an isomerization reactor for converting at least one of orthoxylene, metaxylene, and ethylbenzene to paraxylene.

\* \* \* \* \*